United States Patent
Bernard et al.

(10) Patent No.: US 9,421,353 B2
(45) Date of Patent: Aug. 23, 2016

(54) METHODS OF MANUFACTURING FLEXIBLE POLYMERIC MEDICAL SPIRAL TUBINGS, TUBINGS MADE BY THE METHODS AND USES OF THE TUBINGS

(75) Inventors: Frederic Bernard, Alsgarde (DK); Niels Kornerup, Rungsted (DK); Jesper Schantz Simonsen, Copenhagen (DK)

(73) Assignee: STRYKER EUROPEAN HOLDINGS I, LLC, Kalamazoo, MI (US)

( * ) Notice: Subject to any disclaimer, the term of this patent is extended or adjusted under 35 U.S.C. 154(b) by 3 days.

(21) Appl. No.: 14/344,293

(22) PCT Filed: Sep. 12, 2011

(86) PCT No.: PCT/DK2011/050339
§ 371 (c)(1),
(2), (4) Date: Mar. 11, 2014

(87) PCT Pub. No.: WO2013/037370
PCT Pub. Date: Mar. 21, 2013

(65) Prior Publication Data
US 2014/0371722 A1 Dec. 18, 2014

(51) Int. Cl.
*D01D 5/20* (2006.01)
*A61M 39/08* (2006.01)
*A61M 16/08* (2006.01)
*A61B 18/14* (2006.01)
(Continued)

(52) U.S. Cl.
CPC .......... *A61M 39/08* (2013.01); *A61B 18/1492* (2013.01); *A61M 3/0283* (2013.01);
(Continued)

(58) Field of Classification Search
CPC . B29C 49/0015; B29C 43/22; B29C 43/224; B29C 43/226; B29C 53/30; B29C 61/08
See application file for complete search history.

(56) References Cited

U.S. PATENT DOCUMENTS 6,367,510 B1 4/2002 Carlson
2004/0181174 A2 * 9/2004 Davis ................ A61M 25/0013
600/585
(Continued)

FOREIGN PATENT DOCUMENTS

JP 2001-218851 A 8/2001
JP 2008-036157 A 2/2008
(Continued)

OTHER PUBLICATIONS

JP 2001-218851; Publication Date: Aug. 14, 2001; See English language equivalent U.S. Pat. No. 7,988,656 B2; 36 Pages.
(Continued)

*Primary Examiner* — Stella Yi
(74) *Attorney, Agent, or Firm* — Howard & Howard Attorneys PLLC

(57) ABSTRACT

Methods of manufacturing a length of a flexible polymeric medical tubing of the kind comprising a tubing member defining a lumen, which tubing member is surrounded by spiral convolutions along at least a part of the length of the proximal section and/or the distal section, and which medical tubing has a proximal convoluted section and a distal convoluted section, is disclosed, as well as medical tubings obtained by the methods and their uses. One method comprises the steps of providing a medical tubing wherein the proximal section and the distal section have substantially uniform initial pitch ($P_{initial}$) between adjacent convolutions, and modifying the initial pitch ($P_{initial}$) of at least a part of the proximal section by stretching at least a part of the proximal section to achieve a modified proximal section with a proximal pitch ($P_{proximal}$) between adjacent convolutions that is larger than the initial pitch ($P_{initial}$) between adjacent convolutions. In another method the medical tubing is manufactured in a molding process. The so obtained medical tubing is particularly suited for use in open surgical procedures that requires suction and/or irrigation during use of an electrosurgical instrument.

21 Claims, 1 Drawing Sheet

Figure 1:
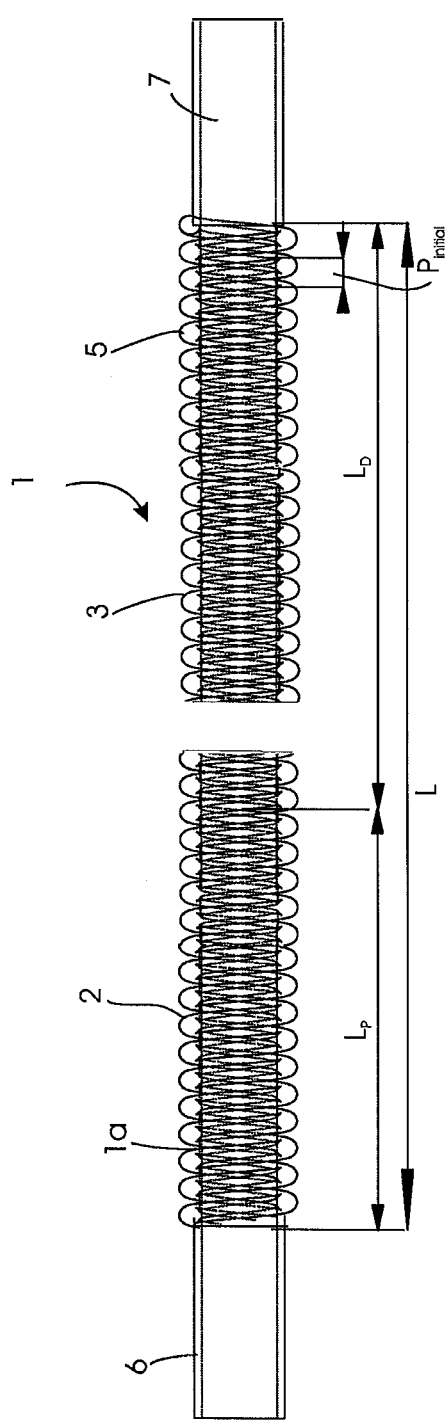

(51) Int. Cl.
*A61M 3/02* (2006.01)
*A61M 25/00* (2006.01)
*B29C 49/00* (2006.01)
*B29D 23/18* (2006.01)
*A61B 18/00* (2006.01)
*B29L 23/00* (2006.01)

(52) U.S. Cl.
CPC ..... *A61M16/0875* (2013.01); *A61M 25/0009* (2013.01); *B29C 49/0015* (2013.01); *B29D 23/18* (2013.01); *A61B 2018/00011* (2013.01); *A61M 2207/00* (2013.01); *B29L 2023/007* (2013.01)

(56) References Cited

U.S. PATENT DOCUMENTS

2005/0131279 A1    6/2005    Boulais et al.
2007/0208300 A1    9/2007    Pravong et al.

FOREIGN PATENT DOCUMENTS

| WO | WO 95/33507 A1 | 12/1995 |
| WO | WO00/00098 * | 1/2000 |
| WO | WO 2007080971 A1 | 7/2007 |

OTHER PUBLICATIONS

English language abstract and machine-assisted English language translation of JP 2008-036157 A extracted from www.espacenet.com on Nov. 6, 2015; 33 pages.

English language abstract and machine-assisted English language translation of WO 2007080971 A1 extracted from www.espacenet.com on Nov. 6, 2015; 74 pages.

* cited by examiner

METHODS OF MANUFACTURING FLEXIBLE POLYMERIC MEDICAL SPIRAL TUBINGS, TUBINGS MADE BY THE METHODS AND USES OF THE TUBINGS

The present invention relates to various methods of manufacturing a length of a flexible polymeric medical tubing of the kind comprising
a tubing member defining a lumen,
which tubing member is surrounded by spiral convolutions along at least a part of the length, and
which medical tubing has a proximal convoluted section and a distal convoluted section.

When performing surgery, in particular open surgery, it is essential to the surgeon to have good working conditions and be able to use a surgical instrument unobstructed and untrammeled and without one or more associated medical tubings get in the way.

In particular if a suction and/or irrigation tubing is combined or associated with the use of the electrosurgical instrument, such tubing takes up space in the vicinity of the surgical site and the surgeon needs to deal with its presence and to avoid getting entangled and/or that something is trapped or catched by a cable and/or the tubing. The tubing adds the feeling of heaviness to the instrument, and put demands on the surgeon's ability to hold and maneuver the instrument during surgery. In particular it may be difficult to perform angular adjustment of the surgical electrode inside the body because of the lack of ability of the tubing to rotate and be moved together with the instrument.

US patent application US 2011/0190768 A1 relating to an electrosurgical instrument with a vacuum port suggests to use a swivel joint as an interface between a bend part on the instrument's pencil-shaped main body and a vacuum outlet port to allow torsional strain to be released.

The swivel joint has a flow channel through which the electrical cable also passes. Thus this prior art solution requires that the electrosurgical instrument is designed to fit intimately together with said swivel joint. The provision of a swivel joint constitutes a both expensive and complicated structure prone to malfunction in case something gets trapped at the swivel joint, as well as an extra assembling and/or manufacturing step in the manufacturing process of the instrument. Moreover, torsional strain is only released very close to the instrument.

For use in irrigation of a surgical site or for evacuating of smoke and/or liquid from a surgical site conventional spiral tubings are able to flex to some extent, but such flexing permits almost solely axial elongation and compression of the tubing. Angular movements and rotations of the instrument and release of torsional strain due to the tubing are difficult and often even impossible, although highly attractive, and the presence of the tubing restricts and hampers the surgeon freedom to move around, move the hand holding the instrument, and many other restrictions relating to repositioning the instrument during surgery.

US patent publication no. 2007/208300 A1 proposes a conventional traditionally used thin-walled but generally stiff medical spiral tubing having structural convoluted re-enforcements, in the form of spiral enlargements of the tube diameter, that makes the tubing flexible and kink-free. The wall thickness at the convolutions is the same as of the remaining tubing and convolutions are made with same pitch and distance along the entire length of the tubing. The convolutions allow the tubing to be axially flexible, while the generally stiff wall material enables the tubing to be vacuum-compatible. The increased overall tubing diameter at the convolution sites make the tubing kink-free when being bent or coiled. The thin-walled tubing can be applied for both pressure and vacuum cases because the convolutions re-enforce the tubing regarding radial and axial compression. One manufacturing process for this kind of tubing is blow-molding, where defined lengths of straight tubing are placed in the center of a mold, and positive air pressure is applied while the tube is being heated. As a result, the initially straight tubing expands to take the shape of the mold. Blow extrusion process is suggested to continuous production of the known spiral tubing. In the blow extrusion process a straight tube is extruded and fed into two moving "mold-like" blocks, positive air pressure is applied while the tubing is being extruded to provide said tubing with identical uniform convolutions along the entire length. The "mold-like" blocks are continuously moved on a rotating conveyor assembly resulting in continuous lengths of the medical spiral tubing with uniform pitch.

Since the convolutions of this known medical spiral tubing are provided with the same pitch along the entire length of medical spiral tubing, said medical spiral tubing can be cut to suitable lengths to be used without further modification on a surgical instrument or other medical equipment in order to benefit from it's anti-kinking properties and bendability, however this known tubing is intended to be very rigid. It cannot be twisted or rotated the slightest about it's longitudinal axis due to said rigidity and it is heavy and complicated to use, in particular to use in an open surgical procedure where surrounding free space is limited.

For use in a surgical procedure as a suction tubing associated with evacuation and/or with infusion of smoke, gas and/or liquid from and to a surgical site when using e.g. the electrosurgical instrument disclosed in US patent application US 2011/0190768 A1 or other conventionally instruments not having a swivel joint many surgeons find the above known kind of spiral tubing too rigid and that it lacks sufficient flexibility. The provision of this known kind of suction tubing impedes maneuverability of conventional surgical instruments with attached tubings, in particular in vicinity of the surgical site, and thus close to the patient, and the surgeon is heavily burdened when twisting, turning and angling the instrument with the attached suction tubing in order to get good visibility and proper and unhindered access to the appropriate location at the patient's body. The surgeon needs to use e.g. the wrist and/or forearm, in often needless efforts to accomplish a suitable position and orientation of the electrosurgical instrument because, despite the convoluted structure of the tubing, such design of a suction tubing is still experienced as being very rigid, unflexible and/or unpliable during use, even if a swivel joint is included too.

Thus, there is an unsatisfied need for more flexible, pliable and user-friendly embodiments of medical tubings and less inexpensive and more versatile solutions to achieve release of torsional strain induced by the presence of a medical tubing on a surgical instrument.

Accordingly, there is a keen desire among surgeons for medical tubings that expedite and facilitate easy and ergonomic operation of an electrosurgical smoke and debris producing instrument, to which the medical tubing is attached during surgery, so that it only requires minimum physical effort to reposition the instrument to occupy a convenient orientation of the instrument, relieves the restraint of the surgeon and remedies the previous need for multiple superfluous repositioning operations of the wrist or other parts of his/hers body to deal with the inherent rigidity and weight load of the known rigid spiral tubings and associated surgical instrument.

It is a main aspect according to the present invention to remedy the disadvantages of known medical spiral tubings as well as providing alternatives to known medical spiral tubings by providing a simple, more pliable and more flexible, medical spiral tubing, of the kind mentioned in the opening paragraph, than hitherto known.

It is a second aspect of the present invention to provide a method of modifying a conventional medical spiral tubing to comply with many surgeons demands for more simple, more pliable and more flexible medical spiral tubings of the kind mentioned in the opening paragraph.

It is a third aspect of the present invention to provide a medical spiral tubing that does not feel heavy when used for suction and/or irrigation on a surgical instrument.

It is a fourth aspect of the present invention to provide a medical spiral tubing that does not require excessive and awkward repositioning of the hand, forearm or wrist when used on a surgical instrument.

It is a fifth aspect of the present invention to provide a medical tubing of the kind mentioned in the opening paragraph that releases torsional strain induced to the tubing by the surgeon during surgery when operating a surgical equipment.

It is a sixth aspect of the present invention to provide an electrosurgical instrument provided with a medical tubing of the kind mentioned in the opening paragraph that releases torsional strain.

The novel and unique whereby these and other aspects are achieved according to the present inventions consists in that the method comprises the steps of
  providing a medical tubing wherein the proximal section and the distal section have substantially uniform initial pitch between adjacent convolutions, and
  modifying the initial pitch of at least a part of the proximal section by stretching at least a part of the proximal section to achieve a modified proximal section with a proximal pitch between adjacent convolutions that is larger than the initial pitch between adjacent convolutions.

Emphasis is made that within the scope of the present invention the proximal section and the distal section can have different substantially uniform initial pitch.

Alternatively, the novel and unique whereby these and other aspect are achieved according to the present inventions consists in that the method comprises the steps of
  manufacturing the medical tubing using a polymeric material as starting material in a molding process to provide a medical tubing wherein at least a part of the proximal section has a proximal pitch between adjacent convolutions that is larger than the pitch of adjacent convolutions of the distal section.

Within the context of the present invention the term "pitch" means the axial distance between two corresponding points on two adjacent convolutions of a spiral. The convolutions makes the medical spiral tubing look as it has an exterior thread or is bellow-like, in relation to which thread or bellow-like shape the term "pitch" is used in the present application. The convolutions coil as a helix along the respective part of the length of the medical spiral tubing.

The terms "stretch", "stretched" or "stretching" are used to indicate a permanent and irreversible deformation. The terms "elongate", "elongating" or "elongation" are used to indicate a reversible deformation provided or provideable to a stretched or molded medical spiral tubing. A stretched or molded medical spiral tubing according to the present invention is able to be pulled longer, i.e. be elongated, but is at least to some extent also still able to contract and revert to the condition and state of the stretched or molded medical spiral tubing prior to pulling due to inherent shape memory. The terms "shortening" or "making shorter" are also used to indicate a reversible deformation albeit where the stretched or molded medical spiral tubing is made shorter by compressing it. Once compression is relieved the shortened flexible medical spiral tubing will be inclined, at least to some extent, to revert towards the stretched or molded condition and state due to the inherent shape memory.

The term "proximal section" is used for a section of the length of a medical tubing closest to the surgical instrument while the term "distal section" is used for a section of the length of the medical tubing farthest away from the surgical instrument, usually the section of the medical tubing closest to the vacuum source. A proximal section may extend directly into a distal section or extend into the distal section via an intermediate section, which intermediate section optionally may be without convolutions, as well as said sections may themselves extend into fittings or tubing part for securing to surgical equipments.

By providing the proximal section with a larger pitch than initially present on a conventional medical spiral tubing, the ability of the proximal section of the medical spiral tubing to twist without the surgeons feels it, is increased considerably.

In the first embodiment of the method according to the present invention the proximal section is permanently deformed due to stretching, and thereby made less rigid and restraining. The distance between adjacent convolutions is increased thereby inducing the ability to rotate or twist about the longitudinal axis of the tubing. Thus, the proximal section is due to a simple stretching step provided with the improved ability of being able to twist and turn about the longitudinal axis of the medical spiral tubing, and thus the ability to release torsional strain. The proximal section of the medical spiral tubing according to the present invention is thus made more slack and able to absorb the movements conferred to the tubing and displacement forces applied to the tubing when the surgeon uses the instrument to which the tubing is connected, without the surgeon has noticeable feeling of the presence of said tubing and is affected by it during surgery.

In the second and alternative embodiment to the above first embodiment of a method according to present invention a similar medical tubing, with appropriate and selected pitches at the proximal section and the distal section, is manufactured using a molding process instead of stretching a medical tubing.

It should be understood that it as also feasible and possible to further stretch this molded medical tubing of the second embodiment using the first embodiment of a method according to the present invention to provide the proximal section with additional length and ability to torque.

Thus using medical tubings made by the methods according to the present invention allows torsional restrain to be released and the surgeon to be relieved of the previously heavy burden of the conventional rigid medical spiral tubing because the stretched or molded proximal section inherently adapt and readapt new convenient positions because the stretched proximal section is able to follow the surgeons movements and to twist and torque without the surgeon notice this.

In a preferred embodiment the proximal pitch between adjacent convolutions can be at least 10% larger than the initial pitch between adjacent convolutions, preferably at least 20% larger than the initial pitch between adjacent convolutions, and can more preferred be 30% or larger between adjacent convolutions. The pitch of any section of the length of a medical tubing can expediently be increased by stretching the polymeric material or be made with the appropriate pitch during the molding step.

Stretching can be made manually conferring a suitable graduated scale or meter stick and applying manual tension. Alternatively, stretching can be made in an automatic drawing tool, optionally including suitable software that facilitates control of the stretching step, and allows for manufacturing of customized stretched medical spiral tubings according to the present invention.

Suitable molding processes include but are not limited to extrusion or blow molding, or combinations of these manufacturing methods.

The length of the distal section can be at least double as long as the modified proximal section or the molded proximal section, preferably at least 2 times longer than the modified proximal section or the molded proximal section, and more preferred at least 3 times longer than the modified proximal section or the molded proximal section.

The above intervals for proximal pitch and length of proximal section, irrespective of how the pitch and length have been accomplished, have been determined by the present inventors as particular suited for use with an electrosurgical instrument with integral suction channel, e.g. the electrosurgical instrument described in the applicants co-pending international applications no. PCT/DK2011/050297, PCT/DK2011/050298, PCT/DK2011/050299 and PCT/DK2011/050300.

The above intervals are preferred but shall not be construed as limiting for the scope of the present inventions. In fact other intervals may be more appropriate for some polymeric materials and dimensions of the medical tubing resulting from the methods. Pitch and length may be chosen in consideration of a.o. the physical and chemical properties of the selected polymeric material, including elongation at break and melting point, the thickness of the tubing member between and at the convolutions, and kind of convolutions. The initial pitch of the starting medical tubing in the first embodiment of the method according to the present invention may also be decisive of how much a section, part or length of this tubing can be stretched further without rupturing and compromising ability to resist suction pressure without rupturing.

The method may comprise that any of the proximal section before stretching, the modified proximal section and/or the molded proximal section extend into a straight proximal tubing part adapted to fit onto a first surgical equipment, optionally a surgical instrument, and preferably an electrosurgical instrument.

The distal section may also extend into a straight distal tubing part adapted to fit onto a second surgical equipment, optionally a suction and/or irrigation source. The straight proximal and distal tubing parts serve to ensure a fluid tight fitting onto the relevant surgical equipment.

Suitable permanent deformation to achieve the above preferred intervals for pitch and length of proximal section that effectively release torsional strain can be accomplished if the method comprises to stretch the proximal section at least 10%, more preferred at least 20% and most preferred about 40%.

The total length of the flexible medical spiral tubing can be modified so that the initial length is made at least 5.5% longer, more preferred at least 6.5% longer, even more preferred at least 7.5% longer, and most preferred about 7.8% longer.

A further advantage, in addition to improved operational properties, is that long medical spiral tubings can be made from less material than usually required for a similar conventional spiral medical tubing. Accordingly, polymeric material can be saved, and thus costs reduced. In addition less waste needs to be disposed of, thereby making the stretched or molded medical spiral tubing according to the present invention a further cost and waste attractive alternative to known disposable medical spiral tubings.

Emphasize is made that the advantages of the medical tubings obtained by the present invention, in particular the advantageously improved ability to relieve torsional strain, can be achieved to more or less extent by providing just a short part of a proximal sections with a proximal pitch that is larger than the distal (initial) pitch. In the simplest embodiment the minimum part of the proximal section having a proximal pitch that is larger than the initial pitch of the distal section is defined by the length of the medical tubing corresponding to two adjacent convolutions. The more convolutions of the proximal section that are given or is made with a larger proximal pitch than the initial pitch, the more flexible the proximal section gets, thereby adding to the ability to relieve torsional strain.

The method may comprise not to stretch the distal section because the same level of adaptability and ability to conform to the surgeon's various movements is not required at the distal section. However stretching of the distal section is a possibility, although less required and/or preferred.

If the polymeric material is an elastomeric material, preferably ethylene vinyl acetate, stretching can easily be achieved without the risk that polymeric material between adjacent convolutions ruptures. A suitable polymeric material is Elvax® 560, obtainable for example from Dupont Danmark ApS, Skjøtevej 26, DK-2770 Kastrup. Other polymeric materials for medical tubings can be selected from various kinds of polyethylenes, polyvinyl chlorides, polyurethanes or polypropylene. This list shall not be understood as exhaustive and blendings, and combinations of any of the aforementioned polymeric materials are also foreseen useable.

As examples of radial dimensions of a medical tubing according to the present invention, the internal diameter of the tubing member can e.g. be about 10±0.5 mm and the external diameter, as defined by the convolutions, be about 12±0.5 mm. These diameter are preferred to fit both a 10 mm connection pipe on a vacuum source or an irrigation source, as well as a correspondingly sized connection end of a surgical equipment adapted for evacuation, suction, aspiration and/or irrigation through the medical spiral tubing.

Irrespective of if surgical equipment fits only with particular diameters of medical tubings, suitable medical tubings can easily be made according to the present invention. By selecting an appropriate polymeric materials the optimum medical tubing according to the present invention is made starting either from a commercially obtainable tubing and modifying this one, or by molding the medical tubing from scratch starting as described above from a suitable polymeric material using a molding process. Parameters of the tubing such as interior or exterior diameters, lengths, and pitches are selected in dependency of the selected material in view of the final and intended purpose of the medical tubing keeping in mind e.g. that the polymeric material shall be able to be stretched in the first embodiment of a method without the tubing member wall between the convolutions breaks or ruptures, or the convolution themselves is negative affected, upon force application. Using the second embodiment of a method allows for medical tubing having considerably different diameters at the proximal section and the distal section as well as provision of a selected and preferred tubing wall thickness between adjacent convolutions.

An exemplary flexible medical spiral tubing made according to the present invention may include a straight proximal tubing part, optionally of 30±2.5 mm, adapted to fit onto a first surgical equipment, optionally an electrosurgical instrument, the straight proximal tubing part may extends into a modified proximal section, which modified proximal section has the initial pitch, optionally of about 4 mm, between adjacent convolutions, and an unstretched length, optionally of 470±10 mm, and which proximal section after being stretched has a relaxed proximal length, optionally of 670±10 mm, and a proximal pitch, optionally of about 6 mm, between adjacent convolutions, or alternatively a proximal section is molded with appropriate proximal pitch and length, the modified proximal section or molded proximal section extends into a distal section having the initial pitch, optionally of about 4 mm, between adjacent convolutions and a relaxed distal length, optionally of 2370±10 mm, and the distal section extends into a straight distal tubing part, optionally of 30±2.5 mm, adapted to fit onto a second surgical equipment, optionally a suction and/or irrigation source.

The invention also relates to a flexible, polymeric, medical tubing of the kind having a tubing member surrounded by spiral convolutions along at least a part of the length of the distal section and/or the proximal section, which medical spiral tubing has a proximal convoluted section and a distal convoluted section. At least a part of the proximal section has a proximal pitch between adjacent convolutions that is larger than the pitch between adjacent convolutions of the distal section.

The polymeric flexible medical tubing can be manufactured using the methods described above.

In particular a flexible medical spiral tubing according to the present invention can be defined by a straight proximal tubing part adapted to fit onto a first surgical equipment, optionally an electrosurgical instrument, in one alternative the straight proximal tubing part may extend into a modified proximal section, which modified proximal section has an initial pitch between adjacent convolutions and an unstretched length, and which proximal section after being stretched has a relaxed proximal length and a proximal pitch between adjacent convolutions, or in another alternative a proximal section may be molded with appropriate proximal pitch and length, the modified proximal section or molded proximal section may extend into a distal section having the initial pitch between adjacent convolutions and a relaxed distal length, and the distal section may extend into a straight distal tubing part adapted to fit onto a second surgical equipment, optionally a suction and/or irrigation source.

Such medical tubings according to the present invention conveniently release torsional strain and improve the surgeon's freedom to move at the surgical site, e.g. a surgical instrument to which the medical tubing is connected without being restrained. Moreover, this simple and inexpensive medical tubing can be used at multiple and different kinds of surgical equipments. Thus the need for conventional medical instruments with mechanical features, such as expensive swivel joints, for alleviating the above-discussed disadvantages of prior art instruments and medical tubings, are eliminated. The medical tubing according to the present invention is an inexpensive alternative to known solutions to release torsional strain, moreover it is versatile and not restricted to use with one single instrument. The tubings need not solely be for use as medical tubings, and the methods according to the present invention can be used to manufacture all kinds of tubings arranged for any use where release of torsional strain at or in the vicinity of the tubing's attachment point to the electrosurgical instrument is relevant.

The initial or resulting medical spiral tubing may, as also mentioned above, have a tubing member with an internal diameter of about 10±0.5 mm, and/or an external diameter as defined by the convolutions of about 12±0.5 mm, and/or the distal section may have a wall thickness of about 0.08-0.12 mm, preferably about 0.9-0.11 mm, and most preferred about 0.10, and/or the modified or molded proximal section may have a wall thickness of about 0.04-0.06 mm, preferably about 0.045-0.55 mm and most preferred about 0.5 mm.

The above dimensions and intervals are appropriate for a medical tubing according to the present invention made of a polymeric material that is an elastomeric material, preferably ethylene vinyl acetate, most preferred Elvax® 560.

The invention further relates to the use of a flexible medical spiral tubing as defined above together with an electrosurgical instrument and a vacuum and/or irrigation source, where a cable of the electrosurgical instrument is guided from the electrosurgical instrument to extend inside the flexible medical spiral tubing. The cable may follow the medical tubing all the way to the vacuum and/or irrigation source where it exits the medical spiral tubing as described in the applicants above co-pending international patent application PCT/DK2011/050300, hereby incorporated by reference, or the cable can be externalized prior to reaching the vacuum and/or irrigation source using suitable interconnection and/or fittings.

Conveniently the cable enters the flexible medical spiral tubing at a straight proximal tubing part medical spiral tubing that is secured to the electrosurgical instrument, and exits the flexible medical spiral tubing at a straight distal tubing part of the medical spiral tubing for being connected to a vacuum and/or irrigation source. In this manner the length of the cable is utilized to define the factual length of the flexible medical spiral tubing in that it keeps said flexible medical spiral tubing in a more or less elongated condition, optionally an elongated condition wherein the elongated length is greater than the length of the tubing obtained by the modification step or achieved in the molding step described above.

Figure 2:
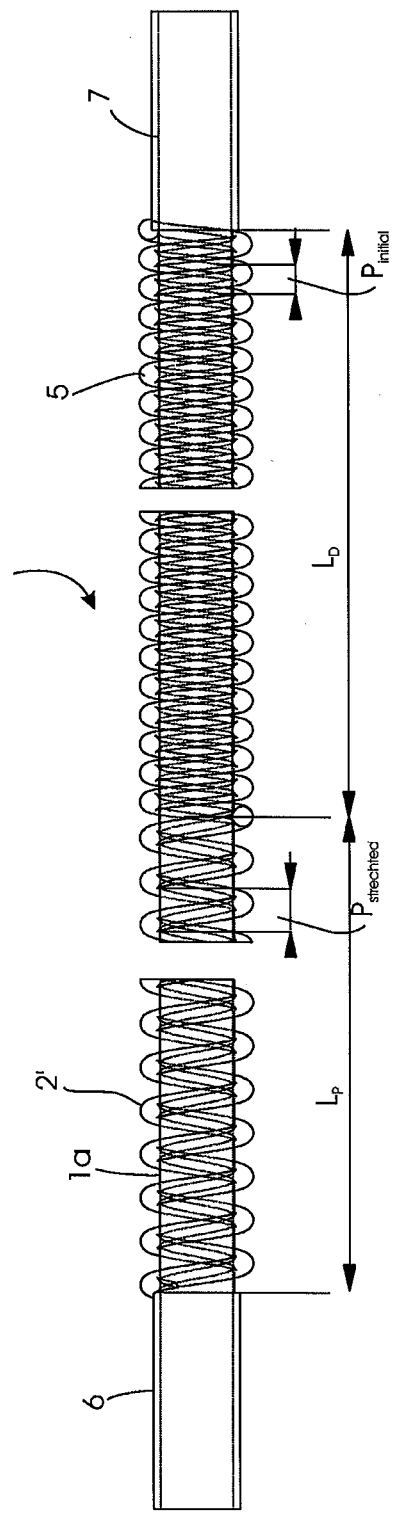

An exemplary embodiment of a flexible medical spiral tubing modified using the first embodiment of a method according to the present invention is schematically shown in the drawing, in which FIG. 1 shows a principle sketch of a conventional medical tubing to be stretched according to the present invention, and FIG. 2 shows the same, stretched according to the method of the present invention, or alternatively obtained using a molding process.

FIG. 1 shows a fragmented view of a medical tubing 1 having a proximal section 2 and a distal section 3. The proximal section and the distal section 3 have uniformly distributed convolutions 5 along the unstretched length L. The convolutions 5 serve to provide anti-kink properties to the conventional tubing 1. The proximal section 2 extends into a straight proximal tubing part 6 adapted to fit onto a first surgical equipment, such as an electrosurgical instrument adapted with suction means (not shown). The distal section 3 extends into a straight distal part tubing part 7 adapted to fit onto a second surgical equipment such as a vacuum means (not shown). In the exemplary embodiment shown in FIGS. 1 and 2 neither the straight proximal tubing part 6 nor the straight distal tubing part 7 have convolutions 5 to ensure optimum sealing properties when connected to respective surgical equipment. Initially the proximal section 2 and the distal section 3 have the same initial pitch $P_{initial}$ between two adjacent convolutions 5 of their entire initial lengths $L_P$ and $L_D$, respectively, wherein $L=L_P+L_D$. Although most preferred, the initial pitch of the proximal section and the distal section, respectively, need not be entirely the same, nor need such initial pitch be the same along the entire length of such section. Any conventionally obtainable tubing can be stretched in accordance with the present invention depending on material properties and dimensions.

FIG. 2 shows that the proximal section 2 of the medical tubing 1 seen in FIG. 1 has been stretched according to the first embodiment of a method of the present invention to achieve a resulting modified medical tubing 1' with a resulting proximal section 2' where the initial pitch $P_{initial}$ is increased to a stretched pitch $P_{stretched}=P_{proximal}$, so that $P_{stretched}>P_{initial}$.

If the medical tubing 1' instead had been manufactured using a molding method, the proximal pitch $P_{proximal}$ and the resulting proximal section 2' and the distal section and the distal pitch, i.e. the initial pitch, could have been achieved directly in the molding process using suitable molds, nozzles, apparatuses, process parameters, polymeric materials, etc. to obtain a similar medical tubing having same mechanical and/or physical properties.

The so obtained medical spiral tubings are particularly suited for use in surgical procedures that requires suction and/or irrigation during use of an electrosurgical instrument wherein the surgeon has improved freedom to move the instruments around without feeling being burdened and hampered.

The invention claimed is:

1. A method of manufacturing a length of a polymeric tubing member, the method comprising:
    providing a polymeric tubing member defining a lumen, where the tubing member is surrounded by spiral convolutions along at least a part of the length (L), and where the tubing member has a proximal convoluted section having a length ($L_P$) and a distal convoluted section having a length ($L_D$), wherein the proximal convoluted section has a substantially uniform initial proximal pitch between adjacent convolutions and the distal convoluted section has a substantially uniform initial distal pitch between adjacent convolutions; and
    modifying the initial proximal pitch of at least a part of the proximal convoluted section by stretching at least a part of the proximal convoluted section to achieve a modified proximal convoluted section with a modified proximal pitch between adjacent convolutions that is larger than the initial proximal pitch between adjacent convolutions;
    wherein the step of modifying the initial proximal pitch modifies an initial total length of the tubing member so that the modified total length is made at least 5.5% longer than the initial total length.

2. The method according to claim 1, wherein the modified proximal pitch between adjacent convolutions is at least 10% larger than the initial proximal pitch between adjacent convolutions.

3. The method according to claim 1, wherein the length ($L_D$) of the distal convoluted section is at least double as long as the modified proximal convoluted section.

4. The method according to claim 1, wherein the modified proximal convoluted section extends into a straight proximal tubing part adapted to fit onto a first surgical equipment.

5. The method according to claim 4, wherein the first surgical equipment is a surgical instrument.

6. The method according to claim 5, wherein the surgical instrument is an electrosurgical instrument.

7. The method according to claim 1, wherein the distal convoluted section extends into a straight distal tubing part adapted to fit onto a second surgical equipment.

8. The method according to claim 7, wherein the second surgical equipment is a suction and/or irrigation source.

9. The method according to claim 1, wherein the step of modifying the initial proximal pitch is further defined as stretching the length ($L_P$) of the proximal convoluted section by at least 10%.

10. The method according to claim 1, wherein the method is free from a step of stretching the distal convoluted section.

11. The method according to claim 1, wherein the method further comprises:
    modifying an initial distal pitch of at least a part of the distal convoluted section by stretching at least a part of the distal convoluted section to achieve a modified distal convoluted section with a modified distal pitch between adjacent convolutions that is larger than the initial distal pitch between adjacent convolutions.

12. The method according to claim 1, wherein the tubing member comprises an elastomeric material.

13. The method according to claim 1, wherein an internal diameter of the tubing member is about 10±0.5 mm and an external diameter, as defined by the convolutions, is about 12±0.5 mm.

14. The method according to claim 4, wherein the distal convoluted section extends into a straight distal tubing part, adapted to fit onto a second surgical equipment.

15. The method according to claim 1, further comprising guiding a cable of an electrosurgical instrument to extend inside the tubing member.

16. The method according to claim 15, wherein the cable enters the tubing member at a straight proximal tubing part that is secured to the electrosurgical instrument and exits the tubing member at a straight distal tubing part connected to a vacuum and/or irrigation source, wherein the length of the cable is utilized to keep said tubing member in an elongated condition.

17. The method according to claim 1, wherein the distal convoluted section has a wall thickness of about 0.08-0.12 mm.

18. The method according to claim 1, wherein the modified proximal section has a wall thickness of about 0.04-0.06 mm.

19. The method according to claim 1, wherein the step of modifying the initial proximal pitch of at least a part of the proximal convoluted section by stretching at least a part of the proximal convoluted section to achieve a modified proximal convoluted section is further defined as permanently and irreversibly deforming at least a part of the proximal convoluted section.

20. A method of manufacturing a length of a polymeric tubing member, the method comprising:

providing a polymeric tubing member defining a lumen, where the tubing member is surrounded by spiral convolutions along at least a part of the length (L), and where the tubing member has a proximal convoluted section having a length ($L_P$) and a distal convoluted section having a length ($L_D$), wherein the proximal convoluted section has a substantially uniform initial proximal pitch between adjacent convolutions and the distal convoluted section has a substantially uniform initial distal pitch between adjacent convolutions;

modifying the initial proximal pitch of at least a part of the proximal convoluted section by stretching at least a part of the proximal convoluted section to achieve a modified proximal convoluted section with a modified proximal pitch between adjacent convolutions that is larger than the initial proximal pitch between adjacent convolutions; and modifying an initial distal pitch of at least a part of the distal convoluted section by stretching at least a part of the distal convoluted section to achieve a modified distal convoluted section with a modified distal pitch between adjacent convolutions that is larger than the initial distal pitch between adjacent convolutions.

21. A method of manufacturing a length of a polymeric tubing member, the method comprising:

providing a polymeric tubing member defining a lumen, where the tubing member is surrounded by spiral convolutions along at least a part of the length (L), and where the tubing member has a proximal convoluted section having a length ($L_P$) and a distal convoluted section having a length ($L_D$), wherein the proximal convoluted section has a substantially uniform initial proximal pitch between adjacent convolutions and the distal convoluted section has a substantially uniform initial distal pitch between adjacent convolutions; and modifying the initial proximal pitch of at least a part of the proximal convoluted section by stretching at least a part of the proximal convoluted section to achieve a modified proximal convoluted section with a modified proximal pitch between adjacent convolutions that is larger than the initial proximal pitch between adjacent convolutions;

wherein the distal convoluted section has a wall thickness of about 0.08-0.12 mm.

\* \* \* \* \*